United States Patent [19]

Los

[11] Patent Number: 4,698,092

[45] Date of Patent: Oct. 6, 1987

[54] 5H-IMIDAZO[2',1':4,3]IMIDAZO-[1,5A]PYRIDIN-6-IUM SALTS AND THEIR USE AS HERBICIDAL AGENTS

[75] Inventor: Marinus Los, Pennington, N.J.

[73] Assignee: American Cynamid Company, Stamford, Conn.

[21] Appl. No.: 822,098

[22] Filed: Jan. 24, 1986

[51] Int. Cl.$^4$ .................. A01N 43/40; C07D 471/14; C07D 221/00
[52] U.S. Cl. ........................................ 71/92; 546/15; 546/64; 546/82
[58] Field of Search ................. 546/64, 82, 15; 71/92

[56] References Cited

U.S. PATENT DOCUMENTS 4,143,142  11/1977  Adhikasy ............................... 546/64

FOREIGN PATENT DOCUMENTS 41623  9/1984  European Pat. Off. ............ 546/82

*Primary Examiner*—John M. Ford
*Assistant Examiner*—J. Richter
*Attorney, Agent, or Firm*—Susan H. Rauch

[57] ABSTRACT

The present invention relates to novel herbicidal pyridinium inner salts and ylides, methods for their preparation and a method for controlling undesirable vegetation utilizing said compounds.

12 Claims, No Drawings

5H-IMIDAZO[2',1':4,3]IMIDAZO-[1,5A]PYRIDIN-6-IUM SALTS AND THEIR USE AS HERBICIDAL AGENTS

BACKGROUND OF THE DISCLOSURE

Herbicidal imidazolin-2-yl pyridine and quinolinecarboxylic acids, esters and salts of formula I below, methods for their preparation and use are described in European Patent Application No. 81103638.3, published Dec. 16, 1981 and pending application for U.S. patent, Ser. No. 616,747, filed June 4, 1984

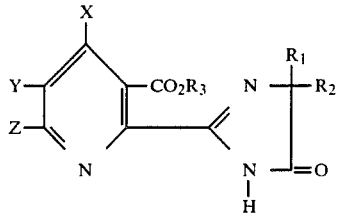

wherein
X is H, halogen, methyl or hydroxyl;
Y and Z are each hydrogen, halogen, $C_1$–$C_6$ alkyl, hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino or $C_1$–$C_4$ alkylsulfonyl group, or phenyl optionally substituted with one $C_1$–$C_4$ alkyl, $C_1$–$C_4$ alkoxy or halogen, difluoromethoxy, trifluoromethoxy, 1,1,2,2-tetrafluoroethoxy, $C_3$–$C_8$ straight or branched alkenyloxy optionally substituted with one to three halogens, or $C_3$–$C_8$ straight or branched alkynyloxy optionally substituted with one to three halogens;
and when taken together, Y and Z may form a ring which may optionally be substituted, in which YZ are represented by —$(CH_2)_n$—, where n is an integer of 3 or 4, or $(CH)_4$;
$R_1$ is $C_1$–$C_4$ alkyl;
$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;
$R_3$ is hydrogen or COOR$_3$ represents a salt or ester of the acid.

SUMMARY OF THE INVENTION

The present invention relates to novel herbicidal (2-imidazolin-2-yl)pyridine and quinolinecarboxylic acid and ester inner salts and ylides, represented by formula II and III below

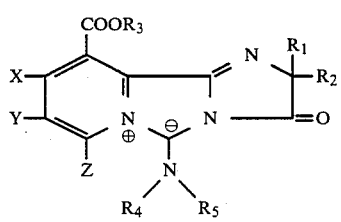

II

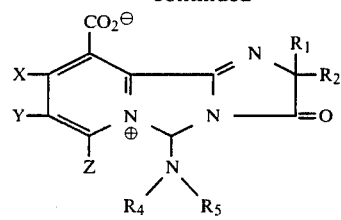

III wherein
X is H, halogen or methyl;
Y and Z are each hydrogen, halogen, $C_1$–$C_6$ alkyl, hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino or $C_1$–$C_4$ alkylsulfonyl group, or phenyl optionally substituted with one $C_1$–$C_4$ alkyl, $C_1$–$C_4$ alkoxy or halogen, difluoromethoxy, trifluoromethoxy, 1,1,2,2-tetrafluoroethoxy, $C_3$–$C_8$ straight or branched alkenyloxy optionally substituted with one to three halogens, or $C_3$–$C_8$ straight or branched alkynyloxy optionally substituted with one to three halogens;
and when taken together, Y and Z may form a ring which may optionally be substituted, in which YZ are represented by —$(CH_2)_n$—, where n is an integer of 3 or 4, or —$(CH)_4$—;
$R_1$ is $C_1$–$C_4$ alkyl;
$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;
$R_3$ is H or COOR$_3$ represents an ester of the acid;
$R_4$ and $R_5$ are each $C_1$–$C_4$ alkyl or phenyl or when taken together, may form a $C_5$ or $C_6$ cycloalkyl;
and when $R_1$ and $R_2$ are not the same the optical isomers thereof.

A preferred group of Formula II and Formula III compounds are those wherein
$R_1$ is $C_1$–$C_4$ alkyl;
$R_2$ is $C_1$–$C_4$ alkyl;
$R_3$ is hydrogen, loweralkyl optionally substituted with phenyl;
$R_4$ is $C_1$–$C_4$ alkyl;
$R_5$ is $C_1$–$C_4$ alkyl or phenyl;
and when $R_4$ and $R_5$ are taken together, they may represent $C_5$–$C_6$ cycloalkyl;
X is H;
Y is hydrogen or $C_1$–$C_4$ loweralkyl;
Z is hydrogen;
and when taken together Y and Z may form a ring represented by —$(CH_2)_4$— or —$(CH)_4$—.

A most preferred group of Formula II and Formula III compounds are those wherein
$R_1$ is methyl; and
$R_2$ is isopropyl.

The novel compounds of the invention are conveniently prepared by the reaction of a Formula I imidazolin-2-yl pyridine or quinolinecarboxylic acid ester or a Formula IV carbamoyl pyridine or quinolinecarboxylic acid ester from which it may be derived with an approximately equimolar amount of a Vilsmeir reagent which is prepared by the reaction of a formamide of Formula V with a chlorinating agent such as phosgene, thionylchloride or POCl$_3$, treatment of the resulting formula II compound with alcoholic base and subsequent acidification yields compounds of formula III as illustrated in Flow Diagram I below.

The reaction is normally conducted in the presence of a chlorinated hydrocarbon solvent such as methylene chloride, dichloroethane, chloroform or the like at ambient temperatures for a period of time sufficient to essentially complete the reaction.

stolons, at rates of from about 0.016 to 4.0 kg/ha, and preferably at rates from about 0.032 to 2.0 kg/ha.

It is of course, obvious that the rates of application above the 4.0 kg/ha level can also be used to effectively kill undesirable plant species; however, rates of application of toxicant above the level necessary to kill the undesirable plants should be avoided since application

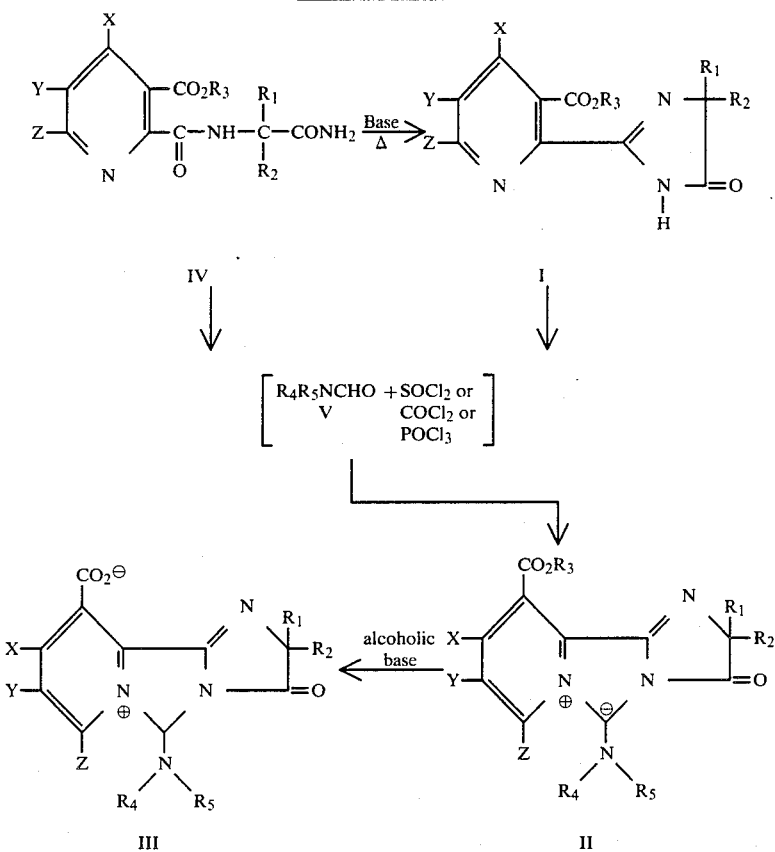

FLOW DIAGRAM I wherein X, Y, Z, $R_1$, $R_2$, $R_3$, $R_4$ and $R_5$ are as defined for Formula II and Formula III above.

The Formula IV carbamoyl and Formula 1 (imidazolin-2-yl)pyridine and quinolinecarboxylic acids and esters suitable for use as intermediates for the preparation of the Formula II and Formula III compounds of the present invention may be prepared by a variety of methods which are described in European Patent Application No. 8110368.3, published Dec. 6, 1981 and pending application for U.S. patent, Ser. Nos. 382,041 and 616,747, which are incorporated herein by reference thereto.

The novel formula II and III (2-imidazolin-2-yl)pyridine and quinolinecarboxylic acid inner salts and ylides of the present invention are exceedingly effective herbicidal agents useful for the control of an exceptionally wide variety of herbaceous and woody annual and perennial monocotyledonous and dicotyledonous plants. Moreover, these compounds are herbicidally effective for controlling weeds indigenous to both dry land and wet land areas. They are also useful as aquatic herbicides and are unique in their effectiveness in controlling the abovesaid plants when applied to the foliage thereof or to soil or water containing seeds or other propagating organs of said plants such as tubers, rhizomes or of excessive amounts of toxicant is costly and serves no useful function in the environment.

Among the plants which may be controlled with the compounds of this invention are: *Elatine triandra, Sagittaria pygmaea, Scirpus hotarui, Cyperus serotinus, Eclipta alba, Cyperus difformis, Rotala indica, Lindernia pyridonoria, Echinochloa crus-galli, Digtaria sanguinalis, Setaria viridis, Cyperus rotundus, Convolvulus arvensis, Agropyron repens, Datura stramonium, Alopercurus myosuroides,* Ipomoea spp., *Sida spinosa, Ambrosia artemisiifolia, Eichornia crassipes, Xanthium pensylvanicum, Sesbania exaltata, Avena fatua, Abutilon theophrasti, Bromus tectorum, Sorghum halepense,* Lolium spp., *Panicum dichotomiflorum,* Matricaria spp., *Amaranthus retroflexus, Cirsium arvense* and *Rumex iaponicus.*

It has been found that the Formula II and III (2-imidazolin-2-yl)pyridine and quinoline compounds are generally selective herbicides, particularly effective for controlling undesirable weeds in the presence of leguminous crops such as soybeans, and cereal crops such as wheat, barley, oats and rye. However, certain compounds are less selective than others in this series.

It has also been found that several of the Formula II and Formula III compounds are effective as antilodging agents in cereal crops when applied at rates of application between about 0.016 to 4.0 kg hectare. At rates of application not exceeding about 0.010 kg per hectare, it has also been found that certain of these compounds are effective for increasing branching of leguminous crops and tillering of cereal crops.

Those Formula II and III compounds which are water soluble, can simply be dispersed in water and applied as a dilute aqueous spray to the foliage of plants or to soil containing propagating organs thereof. These salts also lend themselves to formulation as flowable concentrates.

The compounds also lend themselves to formulation as emulsifiable concentrates, flow concentrates, wettable powders, granular formulation and the like, thus providing a wide range of formulation options for specific purposes.

The formula II and III (2-imidazolin-2-yl)pyridine and quinoline compounds can also be formulated as wettable powders, flow concentrates, granular formulations and the like.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of methyl 10-carboxy-5-(dimethylamino)-2,3-dihydro-2-isopropyl-2-methyl-3-oxo-5H-imidazo[2',1':4,3]imidazo[1,5-a]pyridin-6-ium-5-ylide

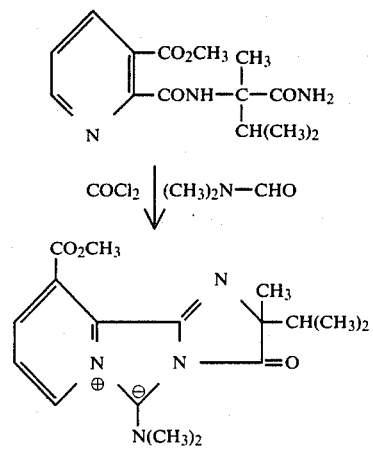

A 12.5% solution of phosgene in benzene (16.5 mL) is added dropwise to a stirred methylene chloride solution (125 mL) of N,N-dimethylformamide (1.18 g). After stirring the resulting precipitate for 45 minutes, solid methyl 2-[(1-carbamoyl-1,2-dimethylpropyl)carbamoyl]nicotinate (5.0 g) is added in portions over a ten minute period and the resulting solution is stirred at ambient temperature overnight. The reaction mixture is washed with a saturated aqueous sodium bicarbonate solution and the aqueous layer separated and extracted with methylene chloride. The organic phases are combined, dried and the solvent removed under reduced pressure. The resulting residue is triturated with diethyl ether to give 2.38 g of the crude title product, which on recrystallization from a methylene chloride-hexane mixture has mp 193°–195° C. (dec).

EXAMPLE 2

Preparation of methyl 10-carboxy-2,3-dihydro-2-isopropyl-2-methyl-3-oxo-5-(1-pyrrolidinyl)-5H-imidazo[2',1':4,3]-imidazo[1,5-a]pyridin-6-ium-5-ylide

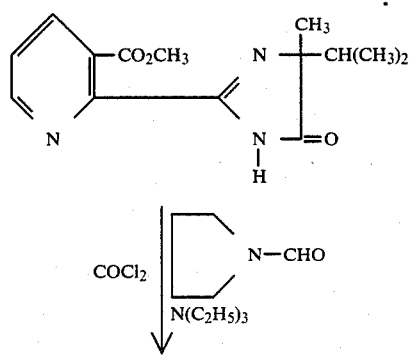

-continued

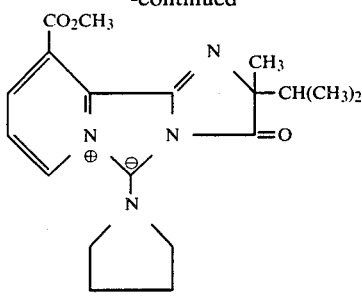

A solution of phosgene in toluene (5.7 mL, 12.5% phosgene, 0.0073 mol) is added dropwise to a stirred solution of pyrrolidine-1-carboxaldehyde (0.76 mL, 0.008 mol) in dry methylene chloride (20 mL) and the resulting mixture allowed to stir for one hour. A methylene chloride (20 mL) solution containing methyl 2-(4-isopropyl-4-methyl-5-oxo-2-imidazolin-2-yl)nicotinate (2.0 g) and triethylamine (1.0 mL) is added over a two minute period and the reaction mixture is then allowed to stand at ambient temperature overnight. Water (50 mL) is added and the mixture allowed to stir for ten minutes. The aqueous phase is separated and the pH adjusted to 5 to 6 with a saturated sodium bicarbonate solution before extracting with methylene chloride. The pH of the separated aqueous phase is adjusted to 8 with saturated sodium bicarbonate before extracting with additional methylene chloride. The organic extracts are combined, dried and concentrated under reduced pressure to give 1.92 g of the title product which after recrystallization from a methylene chloride-hexane mixture has mp 184°–185° C. (dec).

Elemental analysis indicates the product is obtained containing 0.2 H$_2$O.

EXAMPLE 3–10

Preparation of benzyl 10-carboxy-5-(dimethylamino)-2,3-dihydro-2-isopropyl-2-methyl-3-oxo-5H-imidazo[2',1':4,3]imidazo[1,5-a]pyridin-6-ium-5-ylide

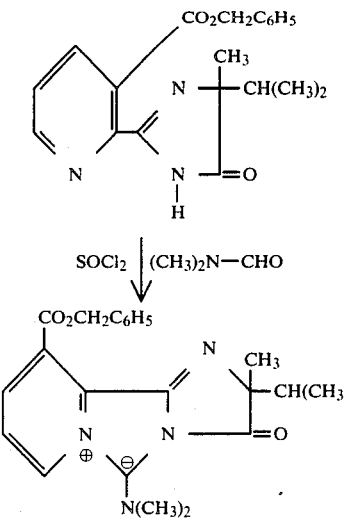

Thionyl chloride (7 mL, 0.096 mol) is added to a stirred suspension of benzyl 2-(4-isopropyl-4-methyl-5-oxo-2-yl)nicotinate (2.5 g, 0.0071 mol) in chloroform (4 mL). After stirring the mixture for five minutes, N,N-dimethylformamide (1.51 g, 0.021 mol) is added and stirring is continued for three hours. The reaction mixture is concentrated under reduced pressure and the residue is treated with ice. The pH of the aqueous mixture is adjusted to 8 with dilute ammonium hydroxide and the basic solution extracted with several portions of diethyl ether. The combined organic extracts are washed with water and the aqueous washes are extracted with methylene chloride. The organic extracts are combined, dried and concentrated in vacuo to afford 2.91 g of the title product, which upon recrystallization from an acetone-ether mixture has mp 166° C.

Utilizing the above procedure and substituting the appropriate formamide and (imidazolin-2-yl)pyridine or quinolinecarboxylic acid ester yields the formula II products listed in Table I below.

TABLE I

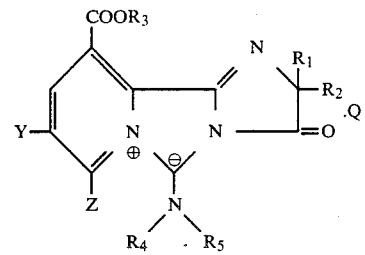

| Example | R$_1$ | R$_2$ | R$_3$ | R$_4$ | R$_5$ | Y | Z | Q | mp °C. |
|---|---|---|---|---|---|---|---|---|---|
| 4 | CH$_3$ | iPr | CH$_3$ | C$_2$H$_5$ | C$_2$H$_5$ | H | H | — | 208–210 |
| 5 | CH$_3$ | iPr | CH$_3$ | —(CH$_2$)$_5$— | | H | H | ⅓H$_2$O | 220–226 (dec) |
| 6 | CH$_3$ | iPr | CH$_3$ | CH$_3$ | CH$_3$ | —CH=CH—CH=CH— | | — | 204–206 |
| 7 | CH$_3$ | iPr | CH$_3$ | CH$_3$ | CH$_3$ | CH$_3$ | H | — | 222–224 |
| 8 | CH$_3$ | iPr | CH$_3$ | CH$_3$ | C$_6$H$_5$ | H | H | H$_2$O | 120–161 (dec) |
| 9 | CH$_3$ | iPr | CH$_3$ | CH$_3$ | CH$_3$ | C$_2$H$_5$ | H | .07CH$_2$Cl | 195–200 (dec) |
| 10 | CH$_3$ | iPr | CH$_3$ | CH$_3$ | CH$_3$ | H | H | — | 120–132 (dec) |

TABLE I-continued

[Structure II shown with COOR₃, N, R₁, R₂, Y, Z, Q, R₄, R₅ substituents]

| Example | R₁ | R₂ | R₃ | R₄ | R₅ | Y | Z | Q | mp °C. |
|---------|----|----|----|----|----|---|---|---|--------|
| (R-isomer) | | | | | | | | | |

EXAMPLE 11

Preparation of 10-carboxy-5-(dimethylamino)-2-dihydro-2-isopropyl-2-methyl-3-oxo-5H-imidazo[2'1':4,3]imidazo[1,5-a]pyridin-6-ium hydroxide inner salt

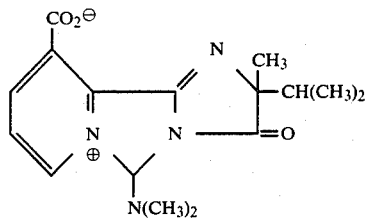

A stirred mixture of the methyl carboxylate ylide (3.5 g, 0.016 mol) and potassium hydroxide (0.84 g, 0.0127 mol) in methanol (50 mL) is heated at 40° C. for two hours. After cooling to ambient temperature the mixture is acidified to pH 4 with dilute methanolic sulfuric acid and then filtered. The filtrate is concentrated in vacuo and the residue is dissolved in methylene chloride. The organic solution is filtered through diatomaceous earth and partially concentrated in vacuo to give a small amount of solid having mp 220° C., which is collected by filtration. Further concentration of the solution yields the title product as the monohydrate (1.58 g, 44%) which after recrystallization from acetone/methylene chloride/hexanes mixture has mp 178°–183° C. Elemental analysis indicates the product is obtained containing 1.0 $H_2O$.

Utilizing the above procedure and substituting the appropriate carboxylate ylide yields the formula I compounds listed in Table II below.

TABLE II

[Structure shown with $CO_2^\ominus$, N, R₁, R₂, Y, Z, Q, R₄, R₅ substituents]

| Example | R₁ | R₂ | R₄ | R₅ | Y | Z | Q | mp °C. |
|---------|----|----|----|----|---|---|---|--------|
| 12 | CH₃ | iPr | C₂H₅ | C₂H₅ | H | H | ¼H₂O | 168–169 |
| 13 | CH₃ | iPr | CH₃ | CH₃ | CH₃ | H | ½H₂SO₄ | 153–158 (dec) |
| 14 | CH₃ | iPr | CH₃ | C₆H₅ | H | H | — | 224–226 (dec) |
| 15 | CH₃ | iPr | CH₃ | CH₃ | —CH=CH—CH=CH— | | ½H₂SO₄ ¼H₂O | 213–215 |
| 16 | CH₃ | iPr | CH₃ | CH₃ | C₂H₅ | H | ¼H₂O | 150–153.5 |
| 17 | CH₃ | iPr | —(CH₂)₅— | | H | H | 1/5 H₂SO₄ ⅓CH₃OH H₂O | 176–178 (dec) |
| 18 | CH₃ (R-isomer) | iPr | CH₃ | CH₃ | H | H | .6H₂SO₄ | 94–135 (dec) |

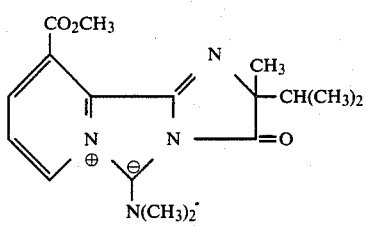

EXAMPLE 19

Postemergence herbicidal evaluation of test compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantity to provide the equivalent of about 0.016 kg to 10 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants are examined and rated according to the rating system provided below. The data obtained are recorded in Table III below.

| Rating System | % Difference in Growth from the Check |
| --- | --- |
| 0 - No effect | 0 |
| 1 - Possible effect | 1-10 |
| 2 - Slight effect | 11-25 |
| 3 - Moderate effect | 26-40 |
| 5 - Definite injury | 41-60 |
| 6 - Herbicidal effect | 61-75 |
| 7 - Good herbicidal effect | 76-90 |
| 8 - Approaching complete kill | 91-99 |
| 9 - Complete kill | 100 |
| 4 - Abnormal growth, that is, a definite physiological malformation but with an over-all effect less than a 5 on the rating scale. | |

In most cases the data are for a single test, but in several instances, they are average values obtained from more than one test.

| Plant Species Used | |
| --- | --- |
| Barnyardgrass | (*Echinochloa crusgalli*) |
| Green foxtail | (*Setaria viridis*) |
| Purple Nutsedge | (*Cyperus rotundus* L.) |
| Wild Oats | (*Avena fatua*) |
| Quackgrass | (*Agropyron repens*) |
| Field Bindweed | (*Convolvulus arvensis* L.) |
| Cocklebur | (*Xanthium pensylvanicum*) |
| Morningglory | (*Ipomoea purpurea*) |
| Ragweed | (*Ambrosia artemisiifolia*) |
| Velvetleaf | (*Abutilon theophrasti*) |

TABLE III

POST-EMERGENCE TESTS - RATES IN KG/HA

| Example Number | RATE | BARN-YARDGR | LARGE CRAB | GREEN FOX | P NUTSEDGE | WILD OATS | QUACK GRASS | FLD BINDWD | COCKLEBUR | MRNGLRY SP | WILD MUSTD | RAGWEED | PRIKY SIDA | VELVET-LEAF |
|---|---|---|---|---|---|---|---|---|---|---|---|---|---|---|
| 1 | 8.000 | 9.0 | 9.0 | 9.0 | 9.0 | 9.0 | 9.0 | 1.0 | 9.0 | 9.0 | 9.0 | 9.0 | 9.0 | 9.0 |
|   | 1.000 |   |   | 9.0 | 8.0 | 9.0 |   | 7.0 | 7.0 | 8.0 | 8.0 | 3.0 |   | 9.0 |
|   | .500 |   |   | 9.0 | 7.0 | 9.0 |   | 7.0 | 6.0 | 8.0 |   | 3.0 |   | 9.0 |
|   | .250 |   |   | 9.0 | 6.0 | 9.0 |   | 7.0 |   | 7.0 |   | 2.0 |   | 9.0 |
|   | .125 |   |   | 8.0 | 1.0 | 7.0 |   | 6.0 |   | 7.0 |   | 0.0 |   | 6.0 |
|   | .063 |   |   | 4.0 | 0.0 | 3.0 |   | 1.0 |   | 6.0 |   | 0.0 |   | 2.0 |
| 2 | 5.000 | 9.0 | 9.0 | 9.0 | 9.0 | 9.0 | 9.0 | 9.0 |   | 8.0 | 9.0 | 9.0 | 9.0 | 8.0 |
|   | 1.000 | 9.0 |   | 9.0 | 7.0 | 9.0 | 8.0 | 6.0 |   | 7.0 |   | 8.0 |   | 8.0 |
|   | .500 | 8.0 |   | 9.0 | 7.0 | 9.0 | 6.0 | 5.0 |   | 7.0 |   | 6.0 |   | 8.0 |
|   | .250 | 3.0 |   | 7.0 | 0.0 | 6.0 | 6.0 | 5.0 |   | 7.0 |   | 4.0 |   | 7.0 |
|   | .125 | 0.0 |   | 3.0 | 0.0 | 1.0 | 2.0 | 5.0 |   | 3.0 |   | 1.0 |   | 3.0 |
| 3 | 1.000 | 9.0 |   |   | 8.0 | 9.0 | 9.0 | 9.0 |   | 9.0 |   | 9.0 |   | 9.0 |
|   | .500 | 9.0 |   |   | 9.0 | 9.0 |   | 9.0 |   | 9.0 |   | 7.0 |   | 9.0 |
|   | .250 | 9.0 |   |   | 8.0 | 9.0 |   | 9.0 |   | 9.0 |   | 2.0 |   | 9.0 |
|   | .125 | 6.0 |   |   | 1.0 | 8.0 | 6.0 | 8.0 |   | 8.0 |   | 2.0 |   | 9.0 |
| 11 | 1.000 | 9.0 |   |   | 0.0 | 9.0 | 4.0 | 6.0 |   | 9.0 |   | 0.0 |   | 6.0 |
|   | .500 | 9.0 |   |   | 8.0 | 9.0 | 9.0 | 9.0 |   | 9.0 |   | 9.0 |   | 9.0 |
|   | .250 | 9.0 |   |   | 8.0 | 9.0 | 6.0 | 9.0 |   | 9.0 |   | 9.0 |   | 9.0 |
|   | .125 | 9.0 |   |   | 4.0 | 9.0 | 6.0 | 9.0 |   | 8.0 |   | 7.0 |   | 9.0 |
|   | .063 | 6.0 |   |   | 2.0 | 9.0 | 6.0 | 7.0 |   | 8.0 |   | 1.0 |   | 7.0 |
|   | .032 | 4.0 |   |   | 0.0 | 6.0 | 6.0 | 7.0 |   | 6.0 |   | 0.0 |   | 4.0 |
| 4 | 1.000 | 8.5 | 9.0 | 9.0 | 6.0 | 8.0 | 6.5 | 7.5 |   | 9.0 | 9.0 | 5.5 |   | 8.0 |
|   | .500 | 7.0 | 8.0 | 9.0 | 6.0 | 7.0 | 7.0 | 7.5 |   | 9.0 | 7.0 | 2.5 |   | 6.5 |
|   | .250 | 6.0* | 4.0 | 5.0 | 0.0 | 6.5 | 3.5* | 6.0 |   | 7.0 | 7.0 | 0.0 |   | 5.0* |
|   | .125 | 3.0 | 4.0 | 5.0 | 0.0 | 3.0* | 3.5* | 2.0 |   | 7.0 | 5.0 | 0.0 |   | 3.5* |
| 5 | 1.000 | 9.0 |   |   | 6.0 | 9.0 | 7.0 | 9.0 |   | 9.0 |   | 9.0 |   | 9.0 |
|   | .500 | 9.0 |   |   | 2.0 | 9.0 | 8.0 | 9.0 |   | 9.0 |   | 6.0 |   | 9.0 |
|   | .250 | 7.0 |   |   | 0.0 | 9.0 | 6.0 | 4.0 |   | 7.0 |   | 2.0 |   | 7.0 |
|   | .125 | 7.0 |   |   | 0.0 | 6.0 | 7.0 | 4.0 |   | 9.0 |   | 0.0 |   | 6.0 |
|   | .063 | 2.0 |   |   | 0.0 | 2.0 | 4.0 | 4.0 |   | 7.0 |   | 0.0 |   | 6.0 |
| 12 | 1.000 | 9.0 |   |   | 9.0 | 9.0 | 9.0 | 8.0 |   | 8.0 |   | 8.0 |   | 8.0 |
|   | .500 | 9.0 |   |   | 8.0 | 9.0 |   | 8.0 |   | 8.0 |   | 4.0 |   | 8.0 |
|   | .250 | 8.0 |   |   | 7.0 | 9.0 |   | 7.0 |   | 8.0 |   | 0.0 |   | 6.0 |
|   | .125 | 8.0 |   |   | 5.0 | 9.0 |   | 5.0 |   | 7.0 |   | 0.0 |   | 2.0 |
|   | .063 | 7.0 |   |   | 2.0 | 9.0 | 7.0 | 4.0 |   | 7.0 |   | 0.0 |   | 2.0 |
| 6 | 1.000 | 6.0 |   |   | 0.0 | 8.0 | 2.0 | 0.0 |   | 0.0 |   | 0.0 |   | 0.0 |
|   | .500 | 2.0 |   |   | 0.0 | 4.0 | 0.0 | 0.0 |   | 0.0 |   | 0.0 |   | 0.0 |
|   | .250 | 9.0 |   |   | 8.0 | 2.0 | 0.0 | 8.0 |   | 8.0 |   | 0.0 |   | 8.0 |
| 7 | 1.000 | 8.0 |   |   | 8.0 | 9.0 | 0.0 | 8.0 |   | 7.0 |   | 4.0 |   | 8.0 |
|   | .500 | 3.0 |   |   | 2.0 | 6.0 | 0.0 | 6.0 |   | 6.0 |   | 4.0 |   | 6.0 |
|   | .250 | 0.0 |   |   | 0.0 | 0.0 | 0.0 | 4.0 |   | 3.0 |   | 0.0 |   | 4.0 |
| 13 | 1.000 | 9.0 |   |   | 9.0 | 9.0 | 4.0 | 9.0 |   | 8.0 |   | 9.0 |   | 9.0 |
|   | .500 | 9.0 |   |   | 9.0 | 9.0 | 1.0 | 8.0 |   | 9.0 |   | 8.0 |   | 9.0 |
|   | .250 | 7.0 |   |   | 8.0 | 9.0 | 0.0 | 7.0 |   | 7.0 |   | 6.0 |   | 6.0 |
|   | .125 | 5.0 |   |   | 7.0 | 4.0 | 0.0 | 4.0 |   | 3.0 |   | 2.0 |   | 4.0 |
|   | .063 | 5.0 |   |   | 7.0 | 9.0 | 9.0 | 7.0 |   | 9.0 |   | 1.0 |   | 2.0 |
| 14 | 1.000 | 8.0 |   |   | 9.0 | 9.0 | 9.0 | 7.0 |   | 9.0 |   | 8.0 |   | 9.0 |
|   | .500 | 8.0 |   |   | 8.0 | 9.0 | 9.0 | 7.0 |   | 9.0 |   | 3.0 |   | 8.0 |

TABLE III-continued

| Example Number | RATE | BARN-YARDGR | LARGE CRAB | GREEN FOX | P NUTSEDGE | WILD OATS | QUACK GRASS | FLD BINDWD | COCKLEBUR | MRNGLRY SP | WILD MUSTD | RAGWEED | PRIKY SIDA | VELVET-LEAF |
|---|---|---|---|---|---|---|---|---|---|---|---|---|---|---|
| | | | | | POST-EMERGENCE TESTS - RATES IN KG/HA | | | | | | | | | |
| | .250 | 9.0 | | | 7.0 | 9.0 | 2.0 | 7.0 | | 8.0 | | 1.0 | | 8.0 |
| | .125 | 8.0 | | | 4.0 | 9.0 | 1.0 | 4.0 | | 4.0 | | 0.0 | | 6.0 |
| 8 | 1.000 | 6.0 | | | 4.0 | 9.0 | 8.0 | 7.0 | | 4.0 | | 0.0 | | 8.0 |
| | .500 | 2.0 | | | 2.0 | 9.0 | 6.0 | 6.0 | | 2.0 | | 0.0 | | 6.0 |
| | .250 | 1.0 | | | 1.0 | 8.0 | 2.0 | 2.0 | | 2.0 | | 0.0 | | 6.0 |
| 15 | 1.000 | 8.0 | | | 4.0 | 9.0 | 8.0 | 4.0 | | 0.0 | | 7.0 | | 4.0 |
| | .500 | 8.0 | | | 1.0 | 9.0 | 8.0 | 2.0 | | 0.0 | | 7.0 | | 2.0 |
| | .250 | 3.0 | | | 0.0 | 9.0 | 2.0 | 1.0 | | 0.0 | | 3.0 | | 1.0 |
| | .125 | 1.0 | | | 0.0 | 6.0 | 1.0 | 0.0 | | 0.0 | | 1.0 | | 0.0 |
| 9 | 1.000 | 8.0 | | | 6.0 | 8.0 | 2.0 | 7.0 | | 0.0 | | 8.0 | | 7.0 |
| | .500 | 6.0 | | | 4.0 | 2.0 | 1.0 | 7.0 | | 0.0 | | 4.0 | | 6.0 |
| | .250 | 2.0 | | | 1.0 | 2.0 | 0.0 | 2.0 | | 0.0 | | 0.0 | | 2.0 |
| 16 | 1.000 | 9.0 | | | 8.0 | 9.0 | 8.0 | 9.0 | | 9.0 | | 9.0 | | 8.0 |
| | .500 | 9.0 | | | 8.0 | 7.0 | 7.0 | 8.0 | | 9.0 | | 8.0 | | 8.0 |
| | .250 | 8.0 | | | 7.0 | 4.0 | 4.0 | 9.0 | | 9.0 | | 3.0 | | 8.0 |
| | .125 | 8.0 | | | 2.0 | 2.0 | 2.0 | 5.0 | | 8.0 | | 2.0 | | 2.0 |
| 10 | 1.000 | 9.0 | | | 8.0 | 9.0 | 9.0 | 9.0 | | 9.0 | | 4.0 | | 9.0 |
| | .500 | 9.0 | | | 9.0 | 9.0 | 9.0 | 7.0 | | 9.0 | | 2.0 | | 9.0 |
| | .250 | 8.0 | | | 6.0 | 8.0 | 9.0 | 7.0 | | 8.0 | | 0.0 | | 9.0 |
| | .125 | 6.0 | | | 5.0 | 6.0 | 7.0 | 6.0 | | 6.0 | | 0.0 | | 8.0 |
| | .063 | 3.0 | | | 0.0 | 4.0 | 7.0 | 5.0 | | 6.0 | | 0.0 | | 6.0 |
| 17 | 1.000 | 9.0 | | | 9.0 | 9.0 | 9.0 | 8.0 | | 9.0 | | 6.0 | | 9.0 |
| | .500 | 9.0 | | | 7.0 | 9.0 | 9.0 | 7.0 | | 9.0 | | 2.0 | | 8.0 |
| | .250 | 8.0 | | | 7.0 | 9.0 | 9.0 | 7.0 | | 7.0 | | 0.0 | | 7.0 |
| | .125 | 8.0 | | | 2.0 | 8.0 | 9.0 | 4.0 | | 7.0 | | 0.0 | | 3.0 |
| | .063 | 4.0 | | | 2.0 | 6.0 | 6.0 | 0.0 | | 4.0 | | 0.0 | | 1.0 |
| 18 | 1.000 | 9.0 | | | 9.0 | 9.0 | 9.0 | 9.0 | | 9.0 | | 8.0 | | 9.0 |
| | .500 | 9.0 | | | 9.0 | 9.0 | 9.0 | 9.0 | | 9.0 | | 6.0 | | 9.0 |
| | .250 | 9.0 | | | 8.0 | 9.0 | 9.0 | 8.0 | | 9.0 | | 2.0 | | 9.0 |
| | .125 | 6.0 | | | 7.0 | 7.0 | 9.0 | 8.0 | | 8.0 | | 2.0 | | 7.0 |
| | .063 | 5.0 | | | 7.0 | 7.0 | 9.0 | 7.0 | | 8.0 | | 0.0 | | 7.0 |
| | .032 | 2.0 | | | 2.0 | 5.0 | 2.0 | 7.0 | | 7.0 | | 0.0 | | 6.0 |

EXAMPLE 20

Preemergence herbicidal evaluation of test compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table IV below. Where more than one test is involved for a given compound, the data are averaged.

TABLE IV

PRE-EMERGENCE TESTS - RATES IN KG/HA

| Example Number | RATE | BARN-YARDGR | LARGE CRAB | GREEN FOX | P NUTSEDGE | WILD OATS | QUACK GRASS | FLD BINDWD | COCKLEBUR | MRNGLRY SP | WILD MUSTD | RAGWEED | PRIKY SIDA | VELVET-LEAF |
|---|---|---|---|---|---|---|---|---|---|---|---|---|---|---|
| 1 | 8.000 | 9.0 | 9.0 | 9.0 | 9.0 | 9.0 | 9.0 | 9.0 | 9.0 | 9.0 | 9.0 | 9.0 | 9.0 | 9.0 |
|  | .500 | 8.0 |  | 9.0 | 9.0 | 9.0 | 9.0 | 9.0 | 9.0 | 8.0 |  | 8.0 |  | 9.0 |
|  | .250 | 7.0 |  | 9.0 | 9.0 | 8.0 | 8.0 | 9.0 | 9.0 | 8.0 |  | 0.0 |  | 9.0 |
|  | .125 | 3.0 |  | 8.0 | 7.0 | 7.0 | 9.0 | 9.0 | 9.0 | 8.0 |  | 0.0 |  | 8.0 |
|  | .063 | 1.0 |  | 4.0 | 5.0 | 0.0 | 1.0 | 9.0 | 7.0 | 1.0 |  | 0.0 |  | 8.0 |
|  | .032 | 0.0 |  | 3.0 | 3.0 | 0.0 | 0.0 | 9.0 | 0.0 | 0.0 |  | 0.0 |  | 2.0 |
|  | .016 | 0.0 |  | 1.0 | 0.0 | 0.0 | 0.0 | 9.0 | 0.0 | 0.0 |  | 0.0 |  | 1.0 |
| 2 | 5.000 | 9.0 | 9.0 | 9.0 | 9.0 | 9.0 | 9.0 | 9.0 |  | 9.0 | 9.0 | 9.0 | 9.0 | 9.0 |
| 3 | .500 | 8.0 |  |  | 9.0 | 9.0 | 9.0 | 9.0 |  | 7.0 |  | 0.0 |  | 9.0 |
|  | .250 | 6.0 |  |  | 9.0 | 2.0 | 9.0 | 9.0 |  | 5.0 |  | 0.0 |  | 8.0 |
|  | .125 | 0.0 |  |  | 0.0 | 0.0 | 3.0 | 8.0 |  | 0.0 |  | 0.0 |  | 7.0 |
|  | .063 | 0.0 |  |  | 0.0 | 0.0 | 0.0 | 2.0 |  | 0.0 |  | 0.0 |  | 5.0 |
|  | .032 | 0.0 |  |  | 0.0 | 0.0 | 0.0 | 0.0 |  | 0.0 |  | 0.0 |  | 3.0 |
|  | .016 | 0.0 |  |  | 0.0 | 0.0 | 0.0 | 0.0 |  | 0.0 |  | 0.0 |  | 0.0 |
| 11 | .500 | 6.0 |  |  | 9.0 | 6.0 | 9.0 | 9.0 |  | 2.0 |  | 0.0 |  | 9.0 |
|  | .250 | 0.0 |  |  | 2.0 | 3.0 | 9.0 | 9.0 |  | 1.0 |  | 0.0 |  | 8.0 |
|  | .125 | 0.0 |  |  | 0.0 | 0.0 | 4.0 | 3.0 |  | 0.0 |  | 0.0 |  | 4.0 |
| 13 | .500 | 8.0 |  |  | 9.0 | 9.0 | 9.0 | 9.0 |  | 8.0 |  | 4.0 |  | 9.0 |
|  | .250 | 4.0 |  |  | 7.0 | 5.0 | 9.0 | 9.0 |  | 7.0 |  | 2.0 |  | 8.0 |
|  | .125 | 3.0 |  |  | 7.0 | 1.0 | 4.0 | 2.0 |  | 6.0 |  | 1.0 |  | 8.0 |
|  | .063 | 0.0 |  |  | 0.0 | 0.0 | 0.0 | 0.0 |  | 2.0 |  | 0.0 |  | 2.0 |
|  | .032 | 0.0 |  |  | 0.0 | 0.0 | 2.0 | 0.0 |  | 0.0 |  | 0.0 |  | 0.0 |
|  | .016 | 0.0 |  |  | 0.0 | 0.0 | 0.0 | 0.0 |  | 0.0 |  | 0.0 |  | 0.0 |
| 14 | .500 | 8.0 |  |  | 4.0 | 8.0 | 9.0 | 9.0 |  | 7.0 |  | 8.0 |  | 9.0 |
|  | .250 | 6.0 |  |  | 2.0 | 7.0 | 9.0 | 3.0 |  | 4.0 |  | 4.0 |  | 8.0 |
|  | .125 | 2.0 |  |  | 2.0 | 3.0 | 8.0 | 0.0 |  | 1.0 |  | 2.0 |  | 3.0 |
| 8 | .500 | 2.0 |  |  | 6.0 | 6.0 | 9.0 | 6.0 |  | 2.0 |  | 0.0 |  | 8.0 |
|  | .250 | 2.0 |  |  | 3.0 | 0.0 | 7.0 | 2.0 |  | 1.0 |  | 0.0 |  | 4.0 |
|  | .125 | 1.0 |  |  | 1.0 | 0.0 | 2.0 | 0.0 |  | 0.0 |  | 0.0 |  | 2.0 |
| 15 | .500 | 4.0 |  |  | 9.0 | 4.0 | 9.0 | 5.0 |  | 0.0 |  | 0.0 |  | 1.0 |
|  | .250 | 2.0 |  |  | 7.0 | 2.0 | 2.0 | 1.0 |  | 5.0 |  | 7.0 |  | 6.0 |
| 9 | .500 | 8.0 |  |  | 6.0 | 0.0 | 4.0 | 8.0 |  | 0.0 |  | 0.0 |  | 3.0 |
|  | .250 | 2.0 |  |  | 4.0 | 0.0 | 0.0 | 8.0 |  | 0.0 |  | 0.0 |  | 7.0 |
| 16 | .500 | 7.0 |  |  | 4.0 | 2.0 | 7.0 | 9.0 |  | 0.0 |  | 0.0 |  | 3.0 |
|  | .250 | 4.0 |  |  | 4.0 | 1.0 | 7.0 | 9.0 |  | 0.0 |  | 0.0 |  | 8.0 |
|  | .125 | 0.0 |  |  | 4.0 | 0.0 | 2.0 | 9.0 |  | 0.0 |  | 0.0 |  | 3.0 |
| 10 | .500 | 8.0 |  |  | 9.0 | 9.0 | 9.0 | 9.0 |  | 8.0 |  | 2.0 |  | 8.0 |
|  | .250 | 5.0 |  |  | 7.0 | 7.0 | 9.0 | 9.0 |  | 8.0 |  | 1.0 |  | 8.0 |
|  | .125 | 2.0 |  |  | 8.0 | 5.0 | 9.0 | 9.0 |  | 4.0 |  | 0.0 |  | 7.0 |
|  | .063 | 1.0 |  |  | 2.0 | 3.0 | 2.0 | 2.0 |  | 1.0 |  | 0.0 |  | 5.0 |
| 17 | .500 | 2.0 |  |  | 7.0 | 2.0 | 9.0 | 9.0 |  | 4.0 |  | 0.0 |  | 6.0 |
|  | .250 | 0.0 |  |  | 2.0 | 2.0 | 9.0 | 2.0 |  | 1.0 |  | 0.0 |  | 2.0 |
|  | .125 | 0.0 |  |  | 1.0 | 0.0 | 2.0 | 8.0 |  | 0.0 |  | 0.0 |  | 1.0 |
| 18 | .500 | 7.0 |  |  | 9.0 | 8.0 | 9.0 | 9.0 |  | 8.0 |  | 2.0 |  | 8.0 |
|  | .250 | 3.0 |  |  | 8.0 | 7.0 | 9.0 | 9.0 |  | 4.0 |  | 1.0 |  | 7.0 |
|  | .125 | 1.0 |  |  | 2.0 | 5.0 | 9.0 | 9.0 |  | 4.0 |  | 0.0 |  | 7.0 |
|  | .063 | 0.0 |  |  | 2.0 | 3.0 | 5.0 | 9.0 |  | 2.0 |  | 0.0 |  | 4.0 |

What is claimed is:
1. (2-imidazolin-2-yl)pyridine and quinolinecarboxylic acid and ester inner salts and ylides, having the structure

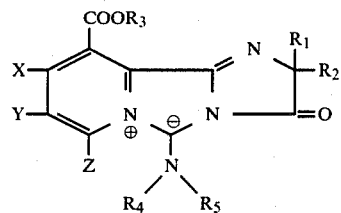 II

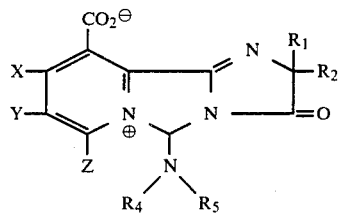 III wherein
X is H, halogen or methyl;
Y and Z are each hydrogen, halogen, $C_1$–$C_6$ alkyl, hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino or $C_1$–$C_4$ alkylsulfonyl group, or phenyl optionally substituted with one $C_1$–$C_4$ alkyl, $C_1$–$C_4$ alkoxy or halogen, difluoromethoxy, trifluoromethoxy, 1,1,2,2-tetrafluoroethoxy, $C_3$–$C_8$ straight or branched alkenyloxy optionally substituted with one to three halogens, or $C_3$–$C_8$ straight or branched alkynyloxy optionally substituted with one to three halogens;
and when taken together, Y and Z may form a ring, in which YZ are represented by —$(CH_2)_n$—, where n is an integer of 3 or 4, or —$(CH)_4$—;
$R_1$ is $C_1$–$C_4$ alkyl;
$R_2$ is $C_1$–$C_4$ alkyl or $C_3$–$C_6$ cycloalkyl; and when $R_1$ and $R_2$ are taken together with the carbon to which they are attached they may represent $C_3$–$C_6$ cycloalkyl optionally substituted with methyl;
$R_3$ is hydrogen or loweralkyl optionally substituted by phenyl;
$R_4$ and $R_5$ are each $C_1$–$C_4$ alkyl or phenyl, or when taken together, may form a piperidine or pyrrolidine ring;
and when $R_1$ and $R_2$ are not the same the optical isomers thereof.

2. A compound according to claim 1 wherein
$R_1$ is $C_1$–$C_4$ alkyl;
$R_2$ is $C_1$–$C_4$ alkyl;
$R_3$ is hydrogen, loweralkyl optionally substitued with phenyl;
$R_4$ is $C_1$–$C_4$ alkyl;
$R_5$ is $C_1$–$C_4$ alkyl or phenyl;
and when $R_4$ and $R_5$ are taken together, they may represent piperidine or pyrrolidine ring;
X is H;
Y is hydrogen or $C_1$–$C_4$ alkyl;
Z is hydrogen;
and when taken together Y and Z may form a ring represented by —$(CH_2)_4$— or —$(CH)_4$—.

3. A compound according to claim 2 wherein $R_1$ is methyl; and $R_2$ is isopropyl.

4. A compound according to claim 3, methyl 10-carboxy-5-(dimethylamino)-2,3-dihydro-2-isopropyl-2-methyl-3-oxo-5H-imidazo[2',1':4,3]-imidazo[1,5-a]pyridin-6-ium-5-ylide and the R isomer thereof.

5. A compound according to claim 3, methyl 10-carboxy-2,3-dihydro-2-isopropyl-2-methyl-3-oxo-5-(1-pyrolidinyl)-5H-imidazo[2',1':4,3]-imidazo[1,5-a]pyridin-6-ium-5-ylide and the R isomer thereof.

6. A compound according to claim 3, benzyl 10-carboxy-5-(dimethylamino)-2,3-dihydro-2-isopropyl-2-methyl-3-oxo-5H-imidazo[2',1':4,3]-imidazo[1,5-a]pyridin-6-ium-5-ylide and the R isomer thereof.

7. A compound according to claim 3, 10-carboxy-5-(dimethylamino)-2,3-dihydro-2-isopropyl-2-methyl-3-oxo-5H-imidazo[2'1':4,3]imidazo[1,5-a]pyridin-6-ium hydroxide inner salt and the R isomer thereof.

8. A compound according to claim 3, 10-carboxy-5-(diethylamino)-2,3-dihydro-2-isopropyl-2-methyl-3-oxo-5H-imidazo[2'1':4,3]imidazo-[1,5-a]pyridin-6-ium hydroxide inner salt and the R isomer thereof.

9. A compound according to claim 3, 10-carboxy-5-(dimethylamino)-2,3-dihydro-2-isopropyl-(2,8-dimethyl)-3-oxo-5H-imidazo[2'1':4,3]imidazo-[1,5-a]pyridin-6-ium hydroxide inner salt and the R isomer thereof.

10. A method for control of monocotyledonous and dicotyledonous annual, perennial and aquatic plant species comprising: applying to the foliage of said plants or to soil or water containing seeds or other propagating organs thereof, a herbicidally effective amount of a compound having a structure:

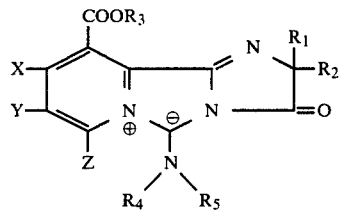 II

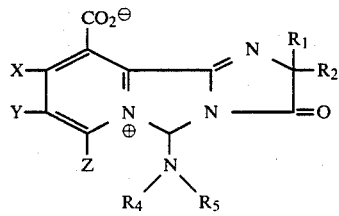 III wherein
X is H, halogen or methyl;
Y and Z are each hydrogen, halogen, $C_1$–$C_6$ alkyl, hydroxyloweralkyl, $C_1$–$C_6$ alkoxy, $C_1$–$C_4$ alkylthio, phenoxy, $C_1$–$C_4$ haloalkyl, nitro, cyano, $C_1$–$C_4$ alkylamino, diloweralkylamino or $C_1$–$C_4$ alkylsulfonyl group, or phenyl optionally substituted with one $C_1$–$C_4$ alkyl, $C_1$–$C_4$ alkoxy or halogen, difluoromethoxy, trifluoromethoxy 1,1,2,2-tetrafluoroethoxy, $C_3$–$C_8$ straight or branched alkenyloxy optionally substituted with one to three halogens, or $C_3$–$C_8$ straight or branched alkynyloxy optionally substituted with one to three halogens;

and when taken together, Y and Z may form a ring, in which YZ are represented by —$(CH_2)_n$—, where n is an integer of 3 or 4, or —$(CH)_4$—;

$R_1$ is $C_1$-$C_4$ alkyl;

$R_2$ is $C_1C_4$ alkyl or $C_3$-$C_6$ cycloalkyl; and when $R_1$ and $R_2$ are taken together with the carbon to which they are attached they may represent $C_3$-$C_6$ cycloalkyl optionally substituted with methyl;

$R_3$ is hydrogen or loweralkyl optionally substituted by phenyl;

$R_4$ and $R_5$ are each $C_1$-$C_4$ alkyl or phenyl, or when taken together, may form a piperidine or pyrrolidine ring;

thereof and when $R_1$ and $R_2$ are not the same the optical isomers thereof.

11. A method according to claim 10 wherein $R_1$ is $C_1$-$C_4$ alkyl;

$R_2$ is $C_1$-$C_4$ alkyl;

$R_3$ is hydrogen or loweralkyl optionally substituted with phenyl;

$R_4$ is $C_1$-$C_4$ alkyl;

$R_5$ is $C_1$-$C_4$ alkyl or phenyl;

and when $R_4$ and $R_5$ are taken together, they may represent piperidine or pyrrolidine ring;

X is H;

Y is hydrogen or $C_1$-$C_4$ loweralkyl;

Z is hydrogen;

and when taken together Y and Z may form a ring represented by —$(CH_2)_4$— or —$(CH)_4$—.

12. A method according to claim 11 wherein $R_1$ is methyl; and $R_2$ is isopropyl.

* * * * *